United States Patent [19]

Broddner et al.

[11] Patent Number: 4,702,242

[45] Date of Patent: Oct. 27, 1987

[54] RESPIRATOR AND/OR ANESTHESIA SUPPLY APPARATUS

[75] Inventors: Sven M. Broddner, Upplands Vasby; Leif Bromster, Solna; Ulf Lundell, Grodinge; Goran S. Pilenvik, Stockholm, all of Sweden

[73] Assignee: Gambro Engstrom AB, Sweden

[21] Appl. No.: 748,772

[22] Filed: Jun. 25, 1985

[30] Foreign Application Priority Data

Jun. 28, 1984 [SE] Sweden .................. 8403450

[51] Int. Cl.$^4$ ........................................ A61M 16/00
[52] U.S. Cl. ........................ 128/205.13; 128/205.14
[58] Field of Search .................. 128/203.14, 205.14, 128/205.15, 205.17, 205.24, 204.18, 205.13

[56] References Cited

U.S. PATENT DOCUMENTS

| | | | |
|---|---|---|---|
| 914,576 | 3/1909 | Jaubert | 128/204.18 |
| 3,045,668 | 7/1962 | Lee | 128/205.15 |
| 3,307,542 | 3/1967 | Andreasen | 128/204.28 |
| 3,467,092 | 9/1969 | Bird et al. | 128/204.25 |
| 3,901,230 | 8/1975 | Henkin | 128/205.15 |
| 4,197,843 | 4/1980 | Bird | 128/203.14 |
| 4,253,453 | 3/1981 | Hay | 128/205.24 |
| 4,267,827 | 5/1981 | Rauscher | 128/205.15 |

FOREIGN PATENT DOCUMENTS 1237273 6/1971 United Kingdom ........... 128/205.15

Primary Examiner—Carlton R. Croyle
Assistant Examiner—Ted Olds
Attorney, Agent, or Firm—Lerner, David, Littenberg, Krumholz & Mentlik

[57] ABSTRACT

Anesthesia or respirator apparatus is disclosed for supplying a gas stream to a patient, including a ventilator for delivering the gas stream, including an inhalation conduit and a compressible bag or bellows, with the gas stream being in contact with the inner surface of the compressible bag and with its outer surface being in contact with a propellant gas stream so that an increase in pressure in the gas stream within the compressible bag can be created by application of the propellant gas against the outer surface of the bag, and including a manual pump associated with the propellant gas stream so that increased pressure can be created in the propellant gas stream, thus resulting in application of the propellant gas stream against the outer surface of the bag, by actuation of the manual pump, and a resultant increase in the pressure in the gas stream within the bag, in turn resulting in an increased flow of the gas stream through the inhalation conduit to the patient.

46 Claims, 2 Drawing Figures

RESPIRATOR AND/OR ANESTHESIA SUPPLY APPARATUS

FIELD OF THE INVENTION

The present invention relates to respirator apparatus and/or apparatus for the supply of anesthesia. More particularly, the present invention relates to such apparatus including a gas preparation section which is adapted to pre-treat a treatment gas, and in particular such a gas which is a mixture of gases from one or more gas sources. Still more particularly, the present invention relates to such apparatus including a normally mechanically operated ventilator section by means of which the prepared gas mixture is then supplied to the patient. Still more particularly, the present invention relates to such apparatus in which the ventilator section is adapted so that it can also be operated with the assistance of a manual reserve system comprising a manually actuated pump.

Yet more particularly, the present invention is primarily intended for use as a complete anesthesia apparatus. It will, however, be clear to those of ordinary skill in this art that in many respects this apparatus can also be applied to apparatus merely intended to be used as a respirator, since many functions of these two types of apparatus are similar in nature.

BACKGROUND OF THE INVENTION

Known anesthesia and/or respirator systems frequently suffer from a disadvantage in that they are technically complicated and therefore become quite expensive. Of course, simpler and/or cheaper systems do exist, but in many cases these systems are then considered to be unreliable. For example, if a manually controlled bag or bellows is directly connected to a duct leading to the patient, a special changeover system would then be required. Furthermore, this would necessitate cleaning between each treatment. In addition, any leakage from such a system would contain dangerous gases.

As an example of a previously known system, reference is made to Swedish Patent No. 168,690. This apparatus, however, as shown in FIG. 1 thereof, includes a bellows 10 as well as a pumping device 15 for externally effecting bellows 10. However, no additional manually operated pump or the like is shown in this apparatus for additional manual control of the pressure to be exerted upon the bellows.

Similarly, the device shown in Swedish Patent Application No. 78.08034-8 includes a pneumatically controlled means 4, but again no separate manually operated bellows or the like is shown therein for controlling same.

SUMMARY OF THE INVENTION

In accordance with the present invention, apparatus has now been discovered for supplying a gas stream to a patient in a manner which overcomes these deficiencies in the prior art. The apparatus includes ventilator means for delivering the gas stream to the patient, the ventilator means including inhalation means comprising inhalation conduit means, a movable wall member having an inner surface and an outer surface, the inner surface being in contact with the gas stream and with the inhalation conduit means, and the outer surface being separated from the gas stream and being in contact with a propellant gas stream, such that an increase in pressure in the gas stream within the inner surface of the movable wall member can be created by the application of the propellant gas stream against the outer surface of the movable wall member, and further including manual pump means associated with the propellant gas stream, such than an increased pressure can be created in the propellant gas stream thus resulting in the application of the propellant gas stream against the outer surface of the movable wall member by the actuation of the manual pump means, and the resultant increase in pressure in the gas stream within the inner surface of the movable wall member, thereby resulting in an increased flow of the gas stream through the inhalation conduit means to the patient.

In accordance with one embodiment of the apparatus of the present invention, the apparatus includes supply means for supplying the gas stream to the ventilator means. Preferably, the gas stream comprises a mixture of a plurality of gases, and the supply means comprises a plurality of gas source means for each of the plurality of gases, and the apparatus further includes mixing means for mixing the plurality of gases to form the gas stream therefrom. In a preferred embodiment, the ventilator means includes exhalation conduit means for removal of an exhaled gas stream from the patient.

In accordance with a preferred embodiment of the apparatus of the present invention, the apparatus includes inhalation transfer conduit means between the inhalation conduit means and for the inner surface of the movable wall member. Preferably, inhalation transfer conduit means includes check valve means for preventing return flow of the gas stream from the inhalation conduit to the inner surface of the movable wall member. In a preferred embodiment, the inhalation transfer conduit means includes throttle means between the check valve means and the inner surface of the movable wall member. In another embodiment, inhalation shunt conduit means are provided connecting the supply means directly to the inhalation conduit means, and supply valve means are provided for selectively supplying the gas stream to either the inhalation shunt means or the inhalation transfer conduit means.

In accordance with another embodiment of the apparatus of the present invention, the apparatus includes propellant gas stream conduit means for supplying at least one of the plurality of gases to the outer surface of the movable wall member as the propellant gas stream. Preferably, reducing valve means are included in the propellant gas stream means for controlling the pressure of the at least one gas being supplied to the outer surface of the movable wall member. In another embodiment, manual pump conduit means are included connecting the manual pump means to the outer surface of the movable wall member, the propellant gas stream conduit means including propellant gas stream valve means, and the manual pump conduit means being connected to a propellant gas stream valve means, whereby the propellant gas stream valve means is actuated upon activation of the manual pump means to open the manual pump conduit means and to simultaneously close the propellant gas stream conduit means.

In accordance with a preferred embodiment of the apparatus of the present invention, the movable wall member comprises a compressible bag member, which is preferably enclosed within a rigid propellant gas stream chamber. Preferably, the compressible bag member comprises a bellows member.

In accordance with another embodiment of the apparatus of the present invention, propellant gas stream conduit means are included for supplying the propellant gas stream to the outer surface of the movable wall member. Preferably, the propellant gas stream conduit means includes relief valve means whereby the existence of a predetermined maximum pressure within the propellant gas stream conduit means causes the relief valve means to open.

In accordance with another embodiment of the apparatus of the present invention, the propellant gas stream valve means has a normal operating condition in which the manual pump conduit means is closed and the propellant gas stream conduit means is open, and the propellant gas stream valve means returns to its normal operating condition between actuations of the propellant gas stream valve means. In a preferred embodiment, inhalation measuring means are included for measuring the flow of the gas stream being supplied to the patient when the propellant gas stream valve means is in its normal operating condition, and for measuring the flow of the gas stream being supplied to the patient when the propellant gas stream valve means is actuated, so that the flow of the gas stream being supplied to the patient can be continuously measured and integrated and compared with a predetermined valve. In a preferred embodiment, inhalation transfer conduit means are included for connecting the inhalation conduit means to the inner surface of the movable well member, and the inhalation transfer conduit means includes the inhalation transfer conduit means includes the inhalation measuring means for measuring the flow of the gas stream in the inhalation transfer conduit means, and wherein the inhalation measuring means comprises a gas flow meter.

By utilization of the present invention, a highly simplified anesthesia and/or respirator apparatus is obtained, while manual operation can be carried out by utilization of a harmless propellant which can be taken from one of the gas sources which are used for preparing the treatment gas itself. This is achieved by adapting the manually actuated pump to act upon the outside of a movable wall in a chamber containing the treatment gas, and preferably to act with the assistance of a gaseous propellant. In any event, the treatment gas and the propellant are thus completely separated from each other.

Preferably, a gas from one of the gas sources utilized for the treatment gas is used as the propellant. It would be evident, however, to those of ordinary skill in this art, that the surrounding air in the atmosphere could also be used for this purpose.

The chamber which contains the treatment gas is appropriately acted upon, as during normal mechanical operation, by the pressure of one of the treatment gases, such as air or oxygen. In this case, the gas is again appropriately taken directly from the source, i.e. before preparation of the treatment gas itself. In order to generate a suitable pressure for this purpose a reducing valve is thus preferably arranged between the source and the chamber whose movable wall is to be acted upon therein.

In accordance with a preferred embodiment of this invention, a changeover valve is also provided in the duct between the gas source and the chamber, and this valve preferably automatically disconnects this gas source when the manually actuated pump is acted on, to produce pressure upon the movable wall.

It will also be evident to those of ordinary skill in this art that the above mentioned chamber can be designed in various ways. Preferably, however, it constitutes a bag, bellows or the like, which is compressible from the outside, and which is in turn arranged in a closed rigid chamber.

For safety reasons the treatment gas and/or propellant for same are appropriately arranged so as to be in connection with a safety valve which opens at the maximum permissible pressure.

A safety and continuous method of operation is thus achieved if the changeover valve is adapted to be automatically reset when manual operation ceases, so that the chamber containing the treatment gas is then once again subjected to normal mechanical operation. This automatic resetting is particulary valuable if the ventilator section is adapted to be controlled according to the so-called EMMV-method (Extended Mandatory Minute Ventilation) in which the inspiratory gas supplied to the patient is continuously measured and integrated and compared with the integral of a corresponding set value. This particular method is described in more detail in U.S. Pat. No. 4,421,113, whose disclosure in this respect is therefore incorporated herein by reference thereto. By utilizing this automatic feedback procedure an operation can be provided in which the inspiratory gas which is also being supplied manually is measured and integrated, and the results obtained are then added to the integral of the mechanically supplied or spontaneously inspirated treatment gas. A rather simple design of this type can be obtained if the mechanically supplied gas and the manually supplied gas are both measured by means of the same meter, which is downstream of the changeover valve.

BRIEF DESCRIPTION OF THE DRAWINGS

The enclosed drawings describe an essentially complete anesthesia arrangement, and in these drawings.

It will be evident to those of ordinary skill in this art that various components of this apparatus can be omitted if one wishes to apply the present invention to an arrangement which is merely intended to be used as a respirator.

DETAILED DESCRIPTION

Figure 1A:
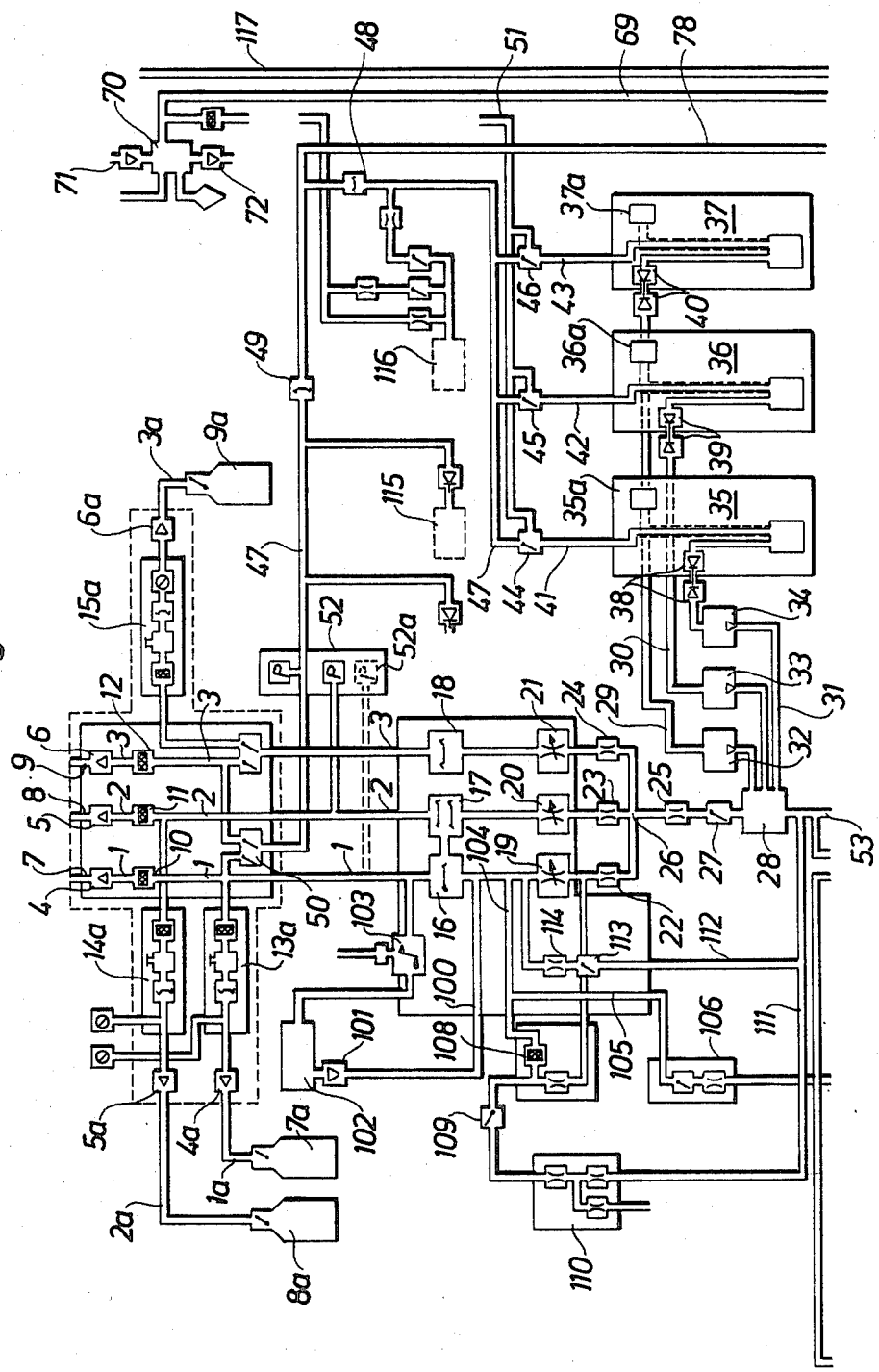
FIG. 1A is a diagramatic, block diagram of a portion of a complete anesthesia arrangement in accordance with the present invention.
Figure 1B:
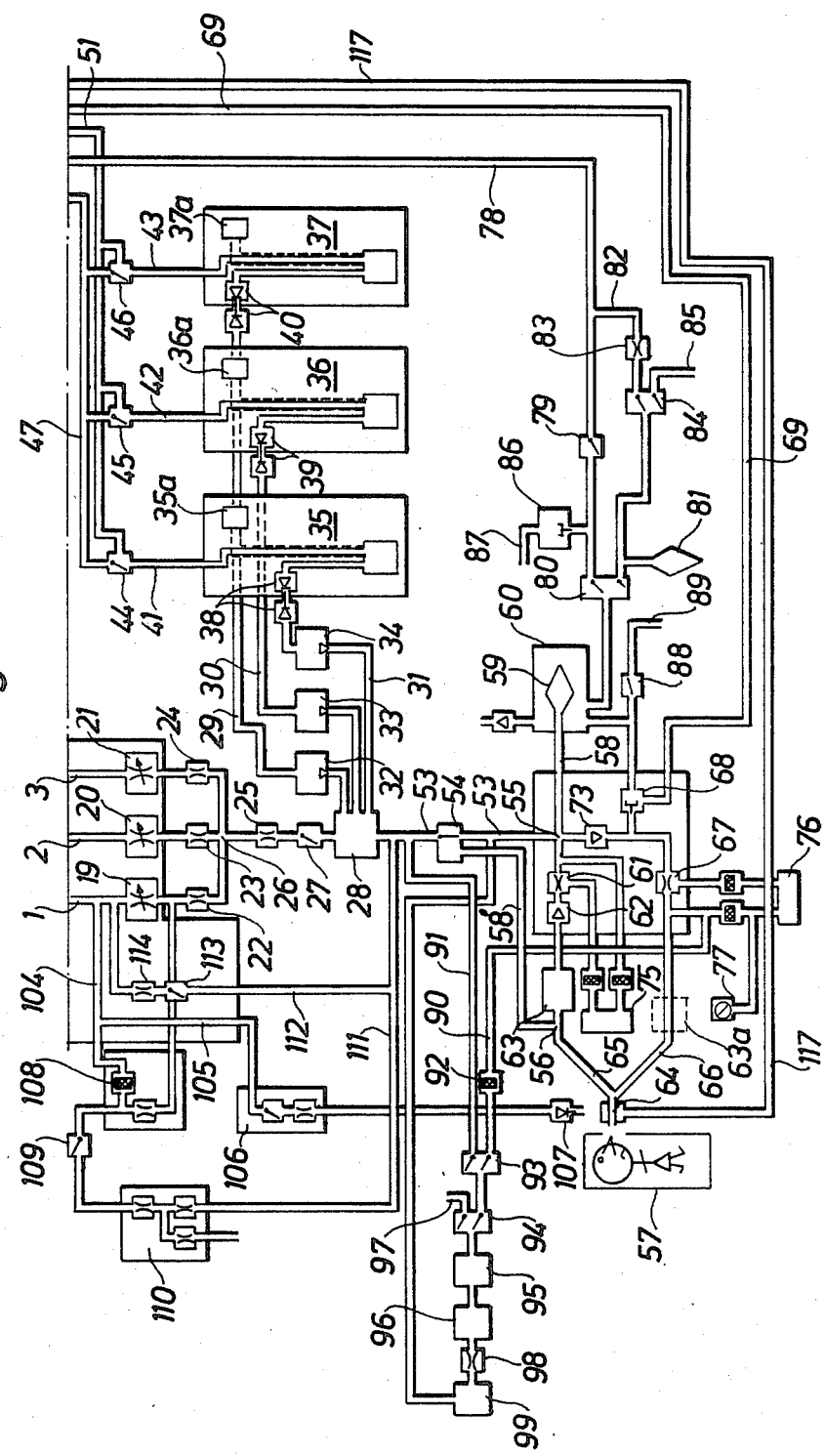
FIG. 1B is a diagramatic, block diagram of the remaining portion of the complete anesthesia arrangement of FIG. 1A in accordance with the present invention.

The present invention can be more fully understood with reference to FIGS. 1A and 1B, which demonstrate a preferred embodiment thereof. Referring to these figures, numerals 1, 2 and 3 designate three parallel inlet ducts which are connected to gas sources (not shown) through attachments 7, 8 and 9 and check valves 4, 5 and 6, respectively. These gas sources may thus constitute fixed installations in a hospital. For filtering out particles, ducts 1, 2 and 3 may contain filters 10, 11 and 12, respectively.

Alternatively, ducts 1, 2 and 3 may instead be connected to separate gas sources, e.g. loose gas tubes 7a, 8a and 9a, through ducts 1a, ab and 1c, respectively. In this case, check valves 4a, 5a and 6a are utilized, as well as the filter and pressure control arrangements which are shown schematically on the drawing, and which as a whole are designated by reference numerals 13a, 14a and 15a.

In the system shown in FIGS. 1A and 1B it is assumed that oxygen gas is to be supplied from sources 7 or 7a and laughing gas ($N_2O$) from sources 8 or 8a. Compressed air is supplied from source 9, and as an alternative, carbon dioxide ($CO_2$) can be supplied from source 9a.

A first pressure control of the gases being supplied takes place in pressure control valves 16, 17 and 18. These valves are then followed by fine control valves, e.g. needle valves 19, 20, and 21. Thereafter, these gas flows are monitored by flow meters 22, 23 and 24, and a further flow meter 25, which is arranged after mixing point 26 for these gases. The cross connection which is shown between valves 16 and 17 indicates that valve 16 is adapted to control valve 17, so that the flow of the gas stream in duct 2 will be dependent, e.q. proportionally, on the gas flow in duct 1.

The gas mixture is then introduced into a gasifier 28 through a valve 27. Liquid is supplied to gasifier 28 through ducts 29, 30 and 31, including valves 32, 33 and 34, from each of three liquid sources 35, 36 and 37, which may contain, for example, halothane, enflurane or isoflurane. These liquid sources can consist of normal glass bottles, which can be connected directly to ducts 29, 30 and 31 through double valves 38, 39 and 40.

Numerals 35a, 36a and 37a designate level gauges for controlling the liquid level in the respective liquid sources.

As is evident from ducts 41, 42 and 43, which include valves 44, 45 and 46, and from duct 47, which includes pressure control valves 48 and 49, the liquid sources 35, 36 and 37 are pressurized with the help of a gas either from duct 1 (i.e. oxygen gas), or duct 3 (i.e. compressed air). The selection between these two gases can be made by means of valve 50.

With the help of valves 44, 45 and 46, the duct 51, liquid sources 35, 36 and 37 can be evacuated when it is not required that they be maintained under pressure. Duct 51 can be appropriately directly connected to the normal evacuation system of a hospital, e.g. via collecting valve 70, which is described in more detail below.

The pressure in duct 2, and in duct 47, respectively, after valve 50, is appropriately read by means of pressure gauge 52, which is shown schematically, and which may also contain a pressure gauge 52a for reading the pressure in duct 1, as shown by broken lines therein.

Gasification suitably occurs in such a manner that one of valves 32, 33 and 34 is periodically opened, with a prescribed frequency, and over a prescribed period of time. In this manner, a prescribed quantity of liquid anesthetic is fed to gasifier 28, where, in accordance with a preferred embodiment of this invention, it is gasified on a heating surface. By monitoring the energy supplied to the heating surface and possibly also its temperature, a further measure of the quantity of liquid being fed is obtained, which can be checked in two ways. With regard to this function, reference is also made to a Swedish patent application entitled "Anaesthesia and/or respirator arrangement with a moistening and/or gasification chamber".

From gasifier 28, the prepared gas mixture is conducted through duct 53, which contains a valve 54, either to a first point 55 or to a second point 56 in a recirculation system, which can be connected to the patient 57. The gas mixture is directly conducted out to point 56 via shunt line 58' if a rapid change of composition of the gas being supplied to the patient is desired. Normally, though, the gas mixture is conducted to point 55, which through duct 58 is connected to a bubble or bellows device 59 contained within a closed housing 60. When the bubble or bellows device 59 is subjected to a pressure, the gas mixture is pressed through a throttle 61, a check valve 62, and possibly a carbon dioxide absorbent 63, through a breathing mask 64 or the like, to the patient. Inspiration takes place here through branch 65, and expiration through branch 66. The expiration takes place through a throttle 67, and an expiration valve 68, which is connected to the evacuation system of the hospital through duct 69 and safety valve 70.

In view of the fact that safety valve 70 is provided with two by-pass valves 71 and 72, the expiratory pressure of the patient can be limited so that it remains within accurately defined limits. For example, valve 71 can be adapted so that it opens when the pressure is below $-1$ cm $H_2O$ and valve 72 opens when the pressure exceeds $+10$ cm $H_2O$.

However, only a small portion of the expiratory gas is normally let out through valve 68. The bulk of this gas is instead recirculated through check valve 73 back to the patient 57. The circulating stream is measured on the one hand over throttle valve 61, and on the other hand over throttle valve 67. This is done with the help of pressure gauges 75 and 76, which are shown schematically in the figures, and which measure the pressure drop over the respective throttle, and consequently the flow through same. As a futher check, flow meter 76 is coordinated with pressure gauge 77.

By means of broken lines, it is indicated that, as an alternative, the carbon dioxide absorbent 63 can be replaced by an absorbent 63a in expiration duct 66.

The propelling force for the bag or bellows device 59 is derived from each of the ducts 1 or 3, through valve 50 and ducts 47 and 78. Duct 78 contains, on the one hand, valve 79, and on the other hand, double valve 80. Valve 79 is controlled in such a manner that pressure is supplied to the housing 60 during the period when inspiration is required. If for any reason it is desired to achieve this manually, it is possible to accomplish this with the help of a second bubble or bellows device 81, which through double valve 80 is also connected to closed housing 60. Valve 80 is adapted so that duct 78 is automatically disconnected when the bubble or bellows device 81 is subjected to a manual pressure in this way. The bubble or bellows device 81 is inflated with the help of a propellant gas from duct 78, through duct 82, with throttle 83 and distributing valve 84. With the help of valve 84 the device can also be vented through evacuation line 85.

Between valves 79 and 80 there is provided a control valve 86, which is shown schematically. With the help of this valve, the so-called PEEP pressure is adjusted, i.e. a certain minimum pressure at the end of a patient's expiratory breath. This valve is also opened should the pressure shown on the pressure gauge 77 be at too high a value. Pressure gauge 77, on the other hand, opens valve 88, through which closed housing 60 is connected to evacuation duct 89.

Samples can be taken through ducts 90 and 91, on the one hand from the patient's expiratory gas, and on the other hand from duct 53 directly after gasifier 28. The duct 90 is connected through a filter 92 and duct 91 directly to a change-over valve 93. Samples are then conducted through a further change-over valve 94 to an anesthesia gas meter 95 and an oxygen gas meter 96. With regard to the design of the anesthesia gas meter, reference is made to the details thereof as set forth in U.S. Pat. No. 4,399,686, which is incorporated herein by reference thereto. Reference is also made to U.S. Pat. No. 4,509,359 regarding the design and function of the ducts.

A calibration gas can also be supplied from connection duct 97 through change-over valve 94. The samples are subsequently sucked back into duct 53 through a throttle 98 with the help of a pump 99.

As a safety measure, treatment gas is withdrawn from duct 1 through duct 100, with check valve 101, to tank 102. Should there be pressure failure in duct 1, this gas is blown out in a known manner through whistle 103.

From duct 1 the treatment gas is also withdrawn through duct 104, duct 105 and a schematically shown pulse generator 106, to a patient connector 107. This connector may consist, for example, of a needle which can be directly introduced into the patient's respiratory passages, and to which a pulsating pressure is supplied at a frequency substantially above that customary in normal breathing, e.g. 10 times above normal. This system is used, for example, when the respiratory passages cannot be reached in any other manner.

The treatment gas may also be conducted from duct 1 through duct 104, filter 108, valve 109 and pressure control device 110, through duct 111 to a point downstream of the gasifier 28. If gas is fed on this route under a strongly reduced pressure with simultaneous pressure measurement the rightness of a ventilator section can be checked. If the pressure does not rise, the leakage is then equal to or greater than the quantity of gas fed.

Through a further shunt line 112, with valve 113 and throttle 114, treatment gas from duct 1 can be led past the gasifier 28. This duct system is used for rapidly flushing the ventilator section free of anesthesia gas. This duct with its throttle and valve is, therefore, of a relatively large dimension, so that such flushing can be achieved rapidly.

By means of designations 115 and 116, together with a number of schematically shown valves and throttles which do not bear designations, the manner in which the treatment gas from duct 47 can be used on the one hand for actuation of a patient suction 115, and on the other hand for inflation of a sleeve belonging to a conventional sphygmomanometer 116.

By means of duct 117 it is indicated how the patient's face mask can be adapted to be directly evacuated. Concerning this function, reference is made to details given in U.S. Pat. No. 4,538,605.

Reference is also made, for example, to U.S. Pat. No. 4,421,113 with regard to the function of the ventilator section, though this can, of course, also be operated in some other known manner.

It is finally noted that the present invention is particularly intended to be used together with the inventions described in U.S. patent applications entitled "Anaesthesia and/or respirator arrangement with multi-purpose utilization of the treatment gas", and "Anaesthesia and/or respirator arrangement with a moistening and-/or gasification chamber" U.S. patent application Ser. No. 748,542, both of which were submitted at the same time. The content of these patent applications is therefore incorporated in the present application by reference thereto.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What we claim is:

1. Apparatus for supplying a gas stream to a patient comprising ventilator means for delivering said gas stream to said patient, said ventilator means including inhalation means comprising inhalation conduit means and exhalation conduit means for removal of an exhaled has stream from said patient, supply means for supplying said gas stream to said ventilator means, a movable wall member having an inner surface and an outer surface, said inner surface of said movable wall member being in contact with said gas stream and with said inhalation conduit means, and said outer surface of said movable wall member being separated from said gas stream and being in contact with a propellant gas stream, whereby an increase in pressure in said gas stream within said inner surface of said movable wall member can be created by the application of said propellant gas stream against said outer surface of said movable wall member, propellant gas stream conduit means for supplying said propellant gas stream to said outer surface of said movable wall member, and manual pump means associated with said propellant gas stream, said manual pump means is inflated in part by said propellant gas whereby an increased pressure can be created in said propellant gas stream, thereby resulting in the application of said propellant gas stream against said outer surface of said movable wall member by the actuation of said manual pump means, and a resultant increase in pressure in said gas stream within said inner surface of said movable wall member, thereby resulting in an increased flow of said gas stream through said inhalation conduit means to said patient.

2. The apparatus of claim 1, wherein said gas stream comprises a mixture of a plurality of gases, and wherein said supply means comprises a plurality of gas source means for each of said plurality of gases, and further including mixing means for mixing said plurality of gases to form said gas stream therefrom.

3. The apparatus of claim 1 including inhalation transfer conduit means between said inhalation conduit means and said inner surface of said movable wall member.

4. The apparatus of claim 3, wherein said inhalation transfer conduit means includes check valve means for preventing return flow of said gas stream from said inhalation conduit to said inner surface of said movable wall member.

5. The apparatus of claim 4, wherein said inhalation transfer conduit means includes throttle means between said check valve means and said inner surface of said movable wall member.

6. The apparatus of claim 4, including inhalation shunt conduit means connecting said supply means directly to said inhalation conduit means, and including supply valve means for selectively supplying said gas stream to either said inhalation shunt means or said inhalation transfer conduit means.

7. The apparatus of claim 1 wherein said movable wall member comprises a compressible bag member.

8. The apparatus of claim 7 including a rigid propellant gas stream chamber, and wherein said compressible bag member is enclosed within said rigid propellant gas stream chamber.

9. The apparatus of claim 7, wherein said compressible bag member comprises a bellows.

10. The apparatus of claim 1, wherein said propellant gas stream conduit means includes relief valve means whereby the existence of a predetermined maximum pressure within said propellant gas stream conduit means causes said relief valve means to open.

11. Apparatus for supplying a gas stream to a patient comprising ventilator means for delivering said gas stream to said patient, said ventilator means including inhalation means comprising inhalation conduit means, a movable wall member having an inner surface and an outer surface, said inner surface of said movable wall member being in contact with said gas stream and with said inhalation conduit means, and said outer surface of said movable wall member being separated from said gas stream and being in contact with a propellant gas stream, whereby an increase in pressure in said gas stream within said inner surface of said movable wall member can be created by the application of said propellant gas stream against said outer surface of said movable wall member, propellant gas stream conduit means for supplying said propellant gas stream to said outer surface of said movable wall member, said propellant gas stream conduit member including propellant gas stream valve means, manual pump means associated with said propellant gas stream, and manual pump conduit means connecting said manual pump means to outer surface of said movable wall member, said manual pump conduit means being connected to said propellant gas stream valve means, said manual pump means is inflated in part by said propellant gas whereby an increased pressure can be created in said propellant gas stream, thereby resulting in the application of said propellant gas stream against said outer surface of said movable wall member by the actuation of said manual pump means, and a resultant increase in pressure in said gas stream within said inner surface of said movable wall member, thereby resulting in an increased flow of said gas stream through said inhalation conduit means to said patient, and whereby said propellant gas stream valve means is actuated upon activation of said manual pump means to open said manual pump conduit means and to simultaneously close said propellant gas stream conduit means.

12. The apparatus of claim 11, including supply means for supplying said gas stream to said ventilator means.

13. The apparatus of claim 12, wherein said gas stream comprises a mixture of a plurality of gases, and wherein said supply means comprises a plurality of gas source means for each of said plurality of gases, and further including mixing means for mixing said plurality of gases to from said gas stream therefrom.

14. The apparatus of claim 12 wherein said ventilator means includes exhalation conduit means for removal of an exhaled gas stream from said patient.

15. The apparatus of claim 14, including inhalation transfer conduit means between said inhalation conduit means and said inner surface of said movable wall member.

16. The apparatus of claim 15, wherein said inhalation transfer conduit means includes check valve means for preventing return flow of said gas stream from said inhalation conduit to said inner surface of said movable wall member.

17. The apparatus of claim 16, wherein said inhalation transfer conduit means includes throttle means between said check valve means and said inner surface of said movable wall member.

18. The apparatus of claim 13, wherein said propellant gas stream conduit means includes supply conduit means for supplying at least one of said plurality of gases to said outer surface of said movable wall member as said propellant gas stream.

19. The apparatus of claim 18, including reducing valve means contained in said propellant gas stream conduit means for controlling the pressure of said at least one gas being supplied to said outer surface of said movable wall member.

20. The apparatus of claim 11, wherein said movable wall member comprises a compressible bag member.

21. The apparatus of claim 20, including a rigid propellant gas stream chamber, and wherein said compressible bag member is enclosed within said rigid propellant gas stream chamber.

22. The apparatus of claim 20, wherein said compressible bag member comprises a bellows.

23. The apparatus of claim 11, including propellant gas stream conduit means for supplying said propellant gas stream to said outer surface of said movable wall member.

24. Apparatus for supplying a gas stream to a patient comprising ventilator means for delivering said gas stream to said patient, said ventilator means including inhalation means comprising inhalation conduit means, a movable wall member having an inner surface and an outer surface, said inner surface of said movable wall member being in contact with said gas stream and with said inhalation conduit means, and said outer surface of said movable wall member being separated from said gas stream and being in contract with a propellant gas stream, whereby an increase in pressure in said gas stream within said inner surface of said movable wall member can be created by the application of said propellant gas stream against said outer surface of said movable wall member, propellant gas stream conduit means for supplying said propellant gas stream to said outer surface of said movable wall member, said propellant gas stream conduit member including propellant gas stream valve means, manual pump means associated with said propellant gas stream, and manual pump conduit means connecting said manual pump means to outer surface of said movable wall member, said manual pump conduit means being connected to said propellant gas stream valve means, such that when pressure is applied to said manual pump means, said manual pump means is inflated in part by said propellant gas, whereby an increased pressure can be created in said propellant gas stream, thereby resulting in the application of said propellant gas stream against said outer surface of said movable wall member by the actuation of said manual pump means, and a resultant increase in pressure in said gas stream within said inner surface of said movable wall member, thereby resulting in an increased flow of said gas stream through said inhalation conduit means to said patient, and whereby said propellant gas stream valve means is actuated upon activation of said manual pump means to open said manual pump conduit means and to simultaneously close said propellant gas stream conduit means.

25. Apparatus for supplying a gas stream to a patient comprising ventilator means for delivering said gas stream to said patient, said ventilator means including inhalation means comprising inhalation conduit means, a movable wall member having an inner surface and an outer surface, said inner surface of said movable wall member being in contact with said gas stream and with said inhalation conduit means, and said outer surface of said movable wall member being separated from said gas stream and being in contract with a propellant gas stream, whereby an increase in pressure in said gas stream within said inner surface of said movable wall member can be created by the application of said propellant gas stream against said outer surface of said movable wall member, inhalation transfer conduit means between said inhalation conduit means and said surface wall member, wherein said inhalation transfer conduit means includes check valve means for preventing return flow of said gas stream from said inhalation conduit to said inner surface of said movable wall member and throttle means between said check valve means and said inner surface of said movable wall member, propellant gas stream conduit means for supplying said propellant gas stream to said outer surface of said movable wall member, said propellant gas stream conduit member including propellant gas stream valve means, and manual pump means associated with said propellant gas stream, and manual pump conduit means connecting said manual pump means to outer surface of said movable wall member, said manual pump conduit means being connected to said propellant gas stream valve means, whereby an increased pressure can be created in said propellant gas stream, thereby resulting in the application of said propellant gas stream against said outer surface of said movable wall member by the actuation of said manual pump means, and a resultant increase in pressure in said gas stream within said inner surface of said movable wall member, thereby resulting in an increased flow of said gas stream through said inhalation conduit means to said patient, and whereby said propellant gas stream valve means is actuated upon activation of said manual pump means to open said manual pump conduit means and to simultaneously close said propellant gas stream conduit means.

26. Apparatus for supplying a gas stream to a patient comprising ventilator means for delivering said gas stream to said patient, said ventilator means including inhalation means comprising inhalation conduit means, a movable wall member having an inner surface and an outer surface, said inner surface of said movable wall member being in contact with said gas stream and with said inhalation conduit means, and said outer surface of said movable wall member being separated from said gas stream and being in contact with a propellant gas stream, whereby an increase in pressure in said gas stream within said inner surface of said movable wall member can be created by the application of said propellant gas stream against said outer surface of said movable wall member, propellant gas stream conduit means for supplying said propellant gas stream to said outer surface of said movable wall member, said propellant gas stream conduit means including relief valve means whereby the existence of a predetermined maximum pressure within said propellant gas stream conduit means causes said relief valve means to open, and manual pump means associated with said propellant gas stream, whereby an increased pressure can be created in said propellant gas stream, thereby resulting in the application of said propellant gas stream against said outer surface of said movable wall member by the actuation of said manual pump means, and a resultant increase in pressure in said gas stream within said inner surface of said movable wall member, thereby resulting in an increased flow of said gas stream through said inhalation conduit means to said patient.

27. The apparatus of claim 26, including supply means for supplying said gas stream to said ventilator.

28. The apparatus of claim 27, wherein said gas stream comprises a mixture of a plurality of gases, and wherein said supply means comprises a plurality of gas source means for each of said plurality of gases, and further including mixing means for mixing said plurality of gases to form said gas stream therefrom.

29. The apparatus of claim 27 wherein said ventilator means includes exhalation conduit means for removal of an exhaled gas stream from said patient.

30. The apparatus of claim 29 including inhalation transfer conduit means between said inhalation conduit means and said inner surface of said movable wall member.

31. The apparatus of claim 30, wherein said inhalation transfer conduit means includes check valve means for preventing return flow of said gas stream from said inhalation conduit to said inner surface of said movable wall member.

32. The apparatus of claim 31, wherein said inhalation transfer conduit means includes throttle means between said check valve means and said inner surface of said movable wall member.

33. The apparatus of claim 31, including inhalation shunt conduit means connecting said supply means directly to said inhalation conduit means, and including supply valve means for selectively supplying said gas stream to either said inhalation shunt means or said inhalation transfer conduit means.

34. The apparatus of claim 28, including propellant gas stream conduit means for supplying at least one of said plurality of gases to said outer surface of said movable wall member as said propellant gas stream.

35. The apparatus of claim 34 including reducing valve means contained in said propellant gas stream conduit means for controlling the pressure of said at least one gas being supplied to said outer surface of said movable wall member.

36. The apparatus of claim 34, including manual pump conduit means connecting said manual pump means to said outer surface means of said movable wall member, said propellant gas stream conduit means including propellant gas stream valve means, and said manual pump conduit means being connected to said propellant gas stream valve means, whereby said propellant gas stream valve means is actuated upon activation of said manual pump means to open said manual pump conduit means and to simultaneously close said propellant gas stream conduit means.

37. The apparatus of claim 26 wherein said movable wall member comprises a compressible bag member.

38. The apparatus of claim 37 including a rigid propellant gas stream chamber, and wherein said compressible bag member is enclosed within said rigid propellant gas stream chamber.

39. The apparatus of claim 37, wherein said compressible bag member comprises a bellows.

40. The apparatus of claim 36, wherein said propellant gas stream valve means has a normal operating condition in which said manual pump conduit means is closed and said propellant gas stream conduit means is open, and wherein said propellant gas stream valve means returns to said normal operating condition between actuations of said propellant gas stream valve means.

41. The apparatus of claim 40, including inhalation measuring means for measuring the flow of said gas stream being supplied to said patient when said propellant gas stream valve means is in normal operating condition, and for measuring the flow of said gas stream being supplied to said patient when said propellant gas stream valve means is actuated, whereby said flow of said gas stream being supplied to said patient can be continuously measured and integrated, and compared with a predetermined value.

42. The apparatus of claim 41, including inhalation transfer conduit means for connecting said inhalation conduit to said inner surface of said movable wall member, and wherein said inhalation transfer conduit means includes said inhalation measuring means for measuring the flow of said gas stream in said inhalation transfer conduit means, said inhalation measuring means comprising a gas flow meter.

43. Apparatus for supplying a gas stream to a patient comprising ventilator means for delivering said gas stream to said patient, said ventilator means including inhalation means comprising inhalation conduit means, a movable wall member having an inner surface and an outer surface, said inner surface of said movable wall member being in contact with said gas stream and with said inhalation conduit means, and said outer surface of said movable wall member being separated from said gas stream and being in contract with a propellant gas stream, whereby an increase in pressure in said gas stream within said inner surface of said movable wall member can be created by the application of said propellant gas stream against said outer surface of said movable wall member, propellant gas stream conduit means for supplying said propellant gas stream to said outer surface of said movable wall member, said propellant gas stream conduit member including propellant gas stream valve means, manual pump means associated with said propellant gas stream, and manual pump conduit means connecting said manual pump means to outer surface of said movable wall member, said manual pump conduit means being connected to said propellant gas stream valve means, whereby an increased pressure can be created in said propellant gas stream, thereby resulting in the application of said propellant gas stream against said outer surface of said movable wall member by the actuation of said manual pump means, and a resultant increase in pressure in said gas stream within said inner surface of said movable wall member, thereby resulting in an increased flow of said gas stream through said inhalation conduit means to said patient, and whereby said gas propellant gas stream valve means is actuated upon activation of said manual pump means to open said manual pump conduit means and to simultaneously close said propellant gas stream conduit means, said propellant gas stream valve means having a normal operating condition to which said manual pump conduit means is closed and said propellant gas stream conduit means is open, and wherein said propellant gas stream valve means returns to said normal operating condition between actuations of said propellant gas stream valve means.

44. The apparatus of claim 43, including inhalation measuring means for measuring the flow of said gas stream being supplied to said patient when said propellant gas stream valve means is in said normal operating condition, and for measuring the flow of said gas stream being supplied to said patient when said propellant gas stream valve means is actuated, whereby said flow of said gas stream being supplied to said patient can be continuously measured and integrated, and compared with a predetermined value.

45. Apparatus for supplying a gas stream to a patient comprising ventilator means for delivering said gas stream to said patient, said ventilator means including inhalation means comprising inhalation conduit means, a movable wall member having an inner surface and an outer surface, said inner surface of said movable wall member being in contact with said gas stream and with said inhalation conduit means, and said outer surface of said movable wall member being separated from said gas stream and being in contract with a propellant gas stream, whereby an increase in pressure in said gas stream within said inner surface of said movable wall member can be created by the application of said propellant gas stream against said outer surface of said movable wall member, propellant gas stream conduit means for supplying said propellant gas stream to said outer surface of said movable wall member, said propellant gas stream conduit member including propellant gas stream valve means, manual pump means associated with said propellant gas stream, wherein said propellant gas stream conduit means includes relief valve means whereby the existence of a predetermined maximum pressure within said propellant gas stream conduit means causes said relief valve means to open, and manual pump conduit means connecting said manual pump means to outer surface of said movable wall member, said manual pump conduit means being connected to said propellant gas stream valve means, whereby an increased pressure can be created in said propellant gas stream, thereby resulting in the application of said propellant gas stream against said outer surface of said movable wall member by the actuation of said manual pump means, and a resultant increase in pressure in said gas stream within said inner surface of said movable wall member, thereby resulting in an increased flow of said gas stream through said inhalation conduit means to said patient, and whereby said propellant gas stream valve means is actuated upon activation of said manual pump means to open said manual pump conduit means and to simultaneously close said propellant gas stream conduit means.

46. The apparatus of claim 44, including inhalation transfer conduit means for connecting said inhalation conduit to said inner surface of said movable wall member, and wherein said inhalation transfer conduit means includes said inhalation measuring means for measuring the flow of said gas stream in said inhalation transfer conduit means, said inhalation measuring means comprising a gas flow meter.

* * * * *

UNITED STATES PATENT AND TRADEMARK OFFICE
CERTIFICATE OF CORRECTION

PATENT NO. : 4,702,242

DATED : October 27, 1987

INVENTOR(S) : Broddner et al

It is certified that error appears in the above-identified patent and that said Letters Patent is hereby corrected as shown below:

Column 2, line 6, "than an" should read -- that an --.

Column 4, line 11, "safety" should read -- safe --.

Column 8, line 12, "has" should read -- gas --.

Column 13, line 59, "to" should read -- in --.

Signed and Sealed this

Tenth Day of May, 1988

Attest:

DONALD J. QUIGG

Attesting Officer

Commissioner of Patents and Trademarks